(12) United States Patent
Young

(10) Patent No.: US 7,351,231 B2
(45) Date of Patent: Apr. 1, 2008

(54) ILLUMINATION ASSEMBLY FOR A CANNULA/HUB ASSEMBLY

(75) Inventor: Christopher S. Young, South Kent, CT (US)

(73) Assignee: ISPG, Inc., New Milford, CT (US)

( * ) Notice: Subject to any disclaimer, the term of this patent is extended or adjusted under 35 U.S.C. 154(b) by 35 days.

(21) Appl. No.: 10/991,838

(22) Filed: Nov. 18, 2004

(65) Prior Publication Data
US 2006/0161117 A1 Jul. 20, 2006

(51) Int. Cl.
A61M 5/00 (2006.01)

(52) U.S. Cl. ...................... 604/264; 604/506
(58) Field of Classification Search ............... 604/264, 604/500, 506; 600/177–178, 223; 601/DIG. 5
See application file for complete search history.

(56) References Cited

U.S. PATENT DOCUMENTS 3,634,938 A * 1/1972 Hutchinson .................. 433/29
4,872,837 A * 10/1989 Issalene et al. ............... 433/29
5,165,387 A * 11/1992 Woodson .................... 600/184
5,672,964 A * 9/1997 Vinci ........................ 324/72.5
6,159,161 A * 12/2000 Hodosh ...................... 600/561

* cited by examiner

Primary Examiner—Nicholas Lucchesi
Assistant Examiner—Theodore J Stigell
(74) Attorney, Agent, or Firm—Carmody & Torrance LLP

(57) ABSTRACT

An illumination assembly for use with a cannula/hub assembly that withdraws fluids from and/or injects fluids into a body. In the preferred embodiment, the illumination assembly comprises a housing and a light-emitting element mounted in and/or on the housing, for emitting directed light to an entry point on the body; wherein the housing is coupled to the cannula/hub assembly such that the location at which the cannula will enter the body remains illuminated even after the cannula has been inserted into the entry point.

15 Claims, 7 Drawing Sheets

ILLUMINATION ASSEMBLY FOR A CANNULA/HUB ASSEMBLY

BACKGROUND OF THE INVENTION

The present invention relates generally to cannula and hub assemblies, and in particular, to an illumination assembly for use therewith, the illumination assembly comprising a light emitting element that emits light that can be directed to a position on a body; wherein in an advantageous way, the location at which the cannula will enter the body (i.e. the entry point) can remain illuminated even after it has been inserted into the entry point. To be sure however, the present invention is also advantageous in other applications where illumination is desirous or necessary, for example for withdrawing fluids from a bottle, as but one example.

Cannula and hub assemblies are well known. During medical procedures, one perceived deficiency in the known assemblies is the inability to illuminate the position on the body (e.g. of a person) at which the cannula will enter (i.e. the entry point). Moreover, after the cannula has been inserted, there are times when it is desirable to maintain illumination on the entry point. For example, the cannula may have "depth" marks so that the practitioner may know how far in the cannula has been inserted; in such an example illumination of such depth marks is important to a successful procedure. During non-medical procedures, often there are instances when illumination is advantageous, such as when trying to extract (or insert) a precision amount of liquid from or to a bottle/container.

One known cannula and hub arrangement with an illumination feature is described in U.S. Pat. No. 4,872,837. However, the illumination feature described therein appears to be less than optimal in procedures where the cannula gets inserted into a bottle, or more likely, into the skin or tissue of the body (e.g. of the patient or person). Specifically, the constructions described in this '837 patent appear to all describe an illumination element (i.e. a small bulb) that emits light which is channeled through the material of the cannula itself. Therefore, it would logically follow that once the cannula is inserted into something, e.g. into the skin or tissue of the body, the emitted light waves can no longer be directed to the point of entry, and thus the lighting condition at the point of cannula insertion is compromised.

It is thus believed that further improvements in illumination during a procedure, such as a medical procedure, are needed. In particular, it would be desirable to provide an illumination assembly that provides for improved and continuous illumination of the location where the cannula has entered, e.g. the skin or tissue of a body, which is especially advantageous during conditions of low lighting, such as during the injection of an epidural, which a practitioner may wish to do under low light conditions to make the ambiance as comforting to the patient as possible.

SUMMARY AND OBJECTS OF THE INVENTION

It is therefore an object of the present invention to provide an improved cannula/hub assembly that includes an illumination assembly that overcomes the foregoing perceived deficiencies.

It is another object of the present invention to provide an improved illumination assembly that provides for improved illumination of an entry point e.g. on a patient's body (preferably but not necessarily of a person), thereby being able to maintain an improved monitoring of a cannula's insertion depth, just to name one example.

Yet another object of the present invention is to provide an improved illumination assembly that provides for improved lighting conditions for a procedure performed during low lighting conditions.

Still other objects and advantages of the invention will in part be obvious and will in part be apparent from the specification.

The invention accordingly comprises the features of construction, combination of elements and arrangement of parts and sequence of steps which will be exemplified in the construction, illustration and description hereinafter set forth, and the scope of the invention will be indicated in the claims.

Therefore, and generally speaking, the present invention is directed to an illumination assembly for use with a cannula/hub assembly that withdraws fluids from and/or injects fluids into a body. In the preferred embodiment, the illumination assembly comprises a housing and a light-emitting element mounted in and/or on the housing, for emitting directed light to an entry point on the body; wherein the housing is coupled to the cannula/hub assembly and the location at which the cannula will enter the body remains illuminated even after the cannula has been inserted into the entry point. An assembly comprising the illumination assembly and the cannula/hub assembly is also provided.

In yet another embodiment, the present invention is particularly applicable for withdrawing fluids from and/or injecting fluids into a container.

BRIEF DESCRIPTION OF THE DRAWINGS

For a fuller understanding of the invention, reference is had to the following description taken in connection with the accompanying figures, in which.

While all features may not be labeled in each Figure, all elements with like reference numerals refer to similar or identical parts.

DETAILED DESCRIPTION OF THE PREFERRED EMBODIMENTS

Generally speaking, the present invention provides many advantages over the prior art, not least of which is the ability to maintain illumination of the entry point of a cannula during a procedure, experimental (e.g. in the laboratory), medical or otherwise. The present invention achieves this advantage by providing an illumination assembly that can be coupled (e.g. integrally, slidably, rotatably and/or removably) to the hub itself and/or to the cannula. Such a construction overcomes a perceived deficiency in the known art, that being the channeling of illumination through the cannula itself, which prevents illumination after the cannula has penetrated a bottle, the skin, tissue, etc. In distinction thereto, the present invention, even after the cannula has entered the entry point, the entry point can remain illuminated and thus provide the practitioner with an improved lighted condition around the cannula's entry point. Other objectives and advantages of the present invention will be discussed below.

As will become clearer below, the cannula/hub assembly, with which the present invention is applicable, may be quite varied, and therefore, specifics made to a particular cannula/hub assembly are by way of example only, and not limitation. With that said, a preferred conventional cannula/hub assembly for use with the present invention is particularly described in co-owned U.S. Pat. No. 6,656,161, the disclosure of which is incorporated by reference as if fully set forth herein.

Figure 1:
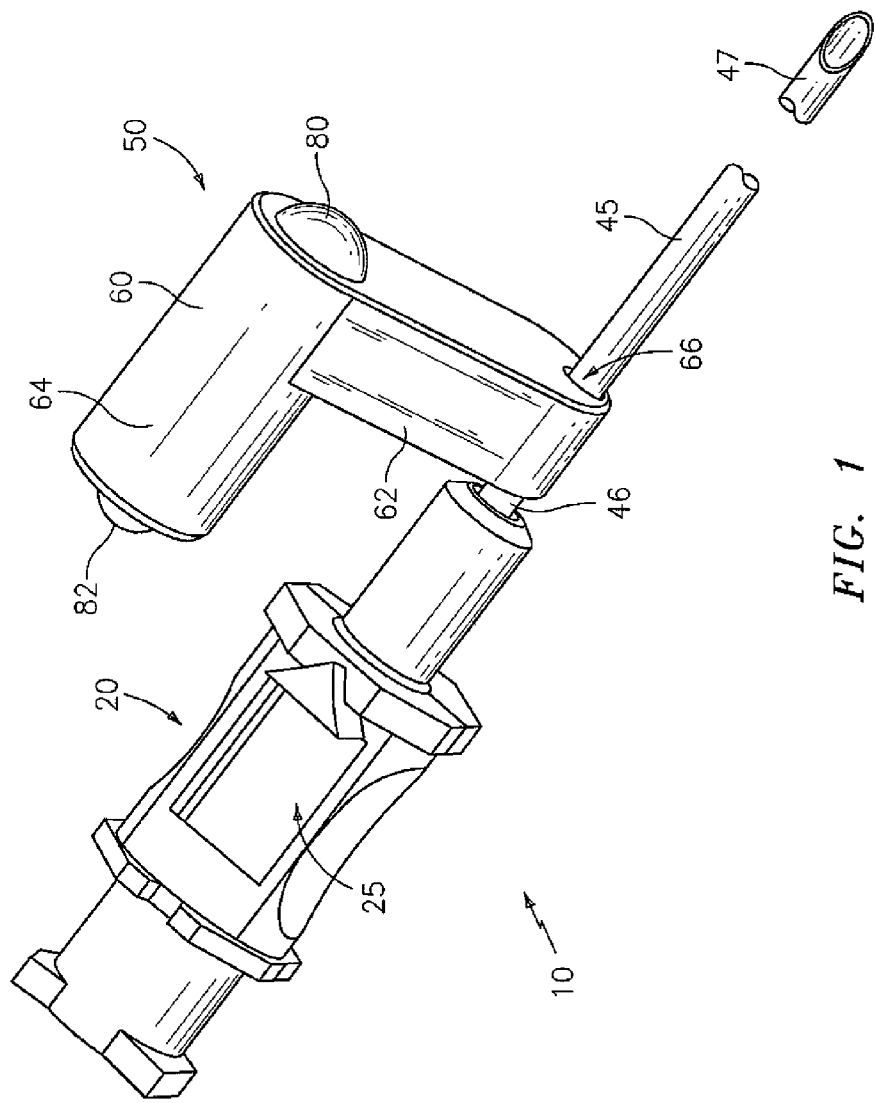
FIG. 1 is a perspective view of an assembly comprising a conventional cannula/hub assembly with an illumination assembly constructed in accordance with a first embodiment of the present invention.
Figure 2:
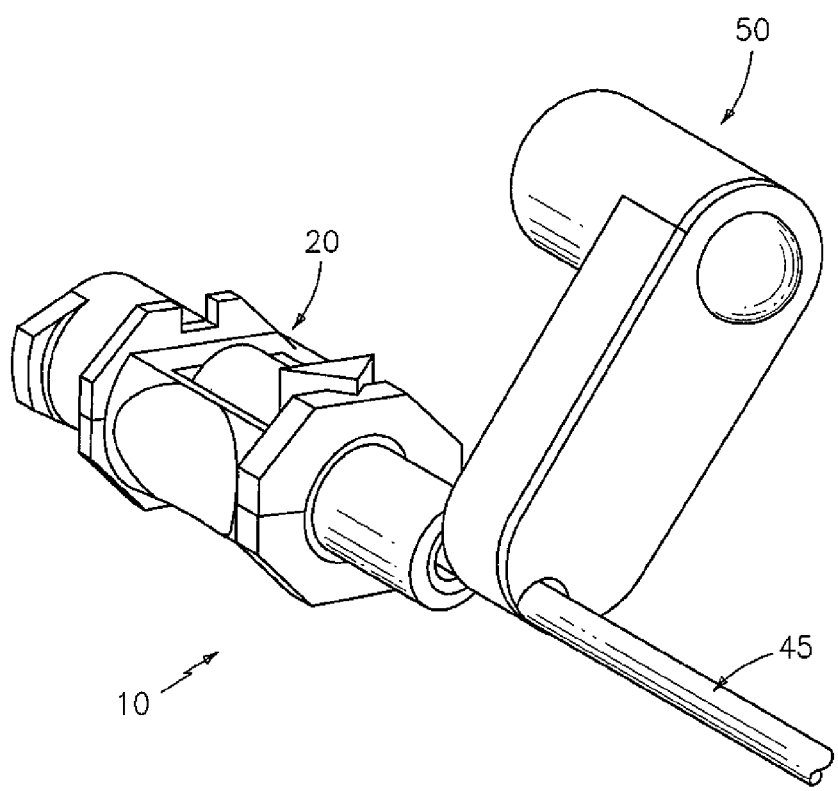
FIG. 2 is a different perspective view of the assembly illustrated in FIG. 1.

Thus, reference is first made to FIGS. 1 and 2 a more detailed description of a first embodiment of the present invention. In particular, FIGS. 1 and 2 illustrate an assembly, generally indicated at 10, comprising a cannula/hub assembly generally indicated at 20 and an illumination assembly generally indicated at 50.

By way of background and for the convenience of the reader, cannula/hub assembly 20 may be utilized in a flashback arrangement, wherein the cannula/hub assembly 20 comprises a hub, generally indicated at 25 and a cannula 45 coupled to hub 25 to permit communication of a bodily fluid (e.g. CSF or blood) with hub 25. Again, by way of example and not limitation, hub 25 may be a magnifying hub as set forth in greater detail in the aforementioned U.S. Pat. No. 6,656,161. For purposes of the present invention, cannula 45 preferably has a first end 46 securable to or within hub 25 and a second end 47 dimensioned to permit withdrawal of the bodily fluid from or inject fluid into a body. Cannula 45 is preferably made of stainless steel and has a pointed, beveled or conically shaped end with a side port entry. Cannula 45 may be affixed to the hub via either medical grade epoxy or insert molding to meet the pull test requirements of ISO 594. The reader is invited to review the aforementioned U.S. Pat. No. 6,656,161 for a more detailed description of other advantages features of a preferred conventional cannula/hub assembly.

Illumination assembly 50 preferably comprises a housing 60 and a light-emitting element 80 mounted in and/or on housing 60. In the embodiment of FIGS. 1 and 2, light-emitting element 80 has one end thereof extending outwardly from housing 60. In this first embodiment, light-emitting element 80 may be battery powered (batteries not shown) and turned "on" and/or "off" by way of a push button 82, such as that positioned on the opposing surface of housing 80. In this way, the batteries and the simple wiring circuit (not shown) to operate light-emitting element 80 may be fully disposed inside housing 80.

Preferably, light-emitting element 80 is of the LED type, and may be one selected from the family of micoLEDs which provide for a desirable amount of light intensity and illumination. Similarly, light-emitting element 80 may be of the laser type for enhanced focusing and pinpoint illumination.

In a preferred embodiment, housing 60 may be a unitary member comprised of a first arm 62 and a second arm 64. First arm 62 may comprise a clip arrangement, generally indicated at 66, for removable coupling to cannula 45. Such a clip arrangement is preferably of the snap-fit type (and removable). In this way, illumination assembly 50 may be removably coupled to cannula/hub assembly when needed or desired for the procedures that can appreciate the advantages provided thereby.

Figure 3:
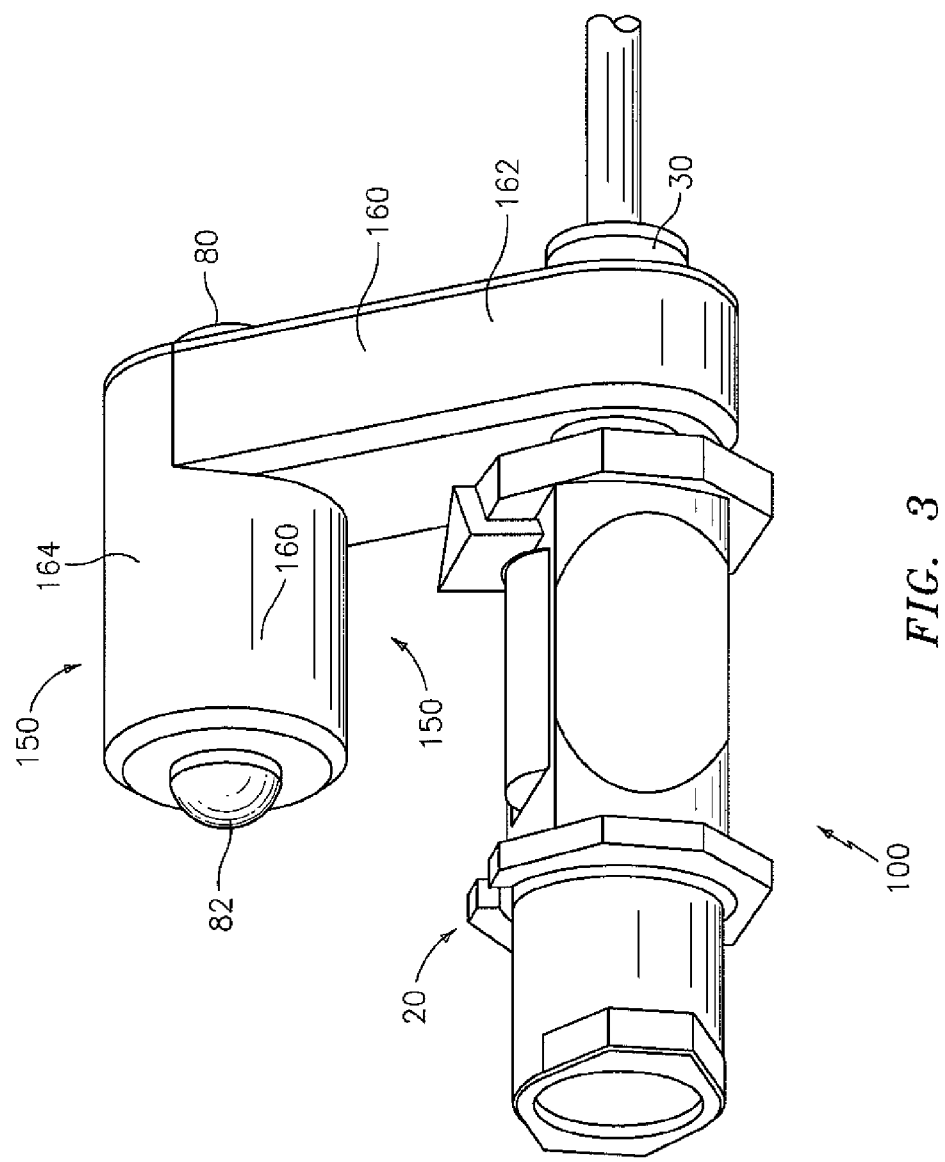
FIG. 3 is a perspective view of an assembly comprising a conventional cannula/hub assembly with an illumination assembly constructed in accordance with a second embodiment of the present invention.
Figure 4:
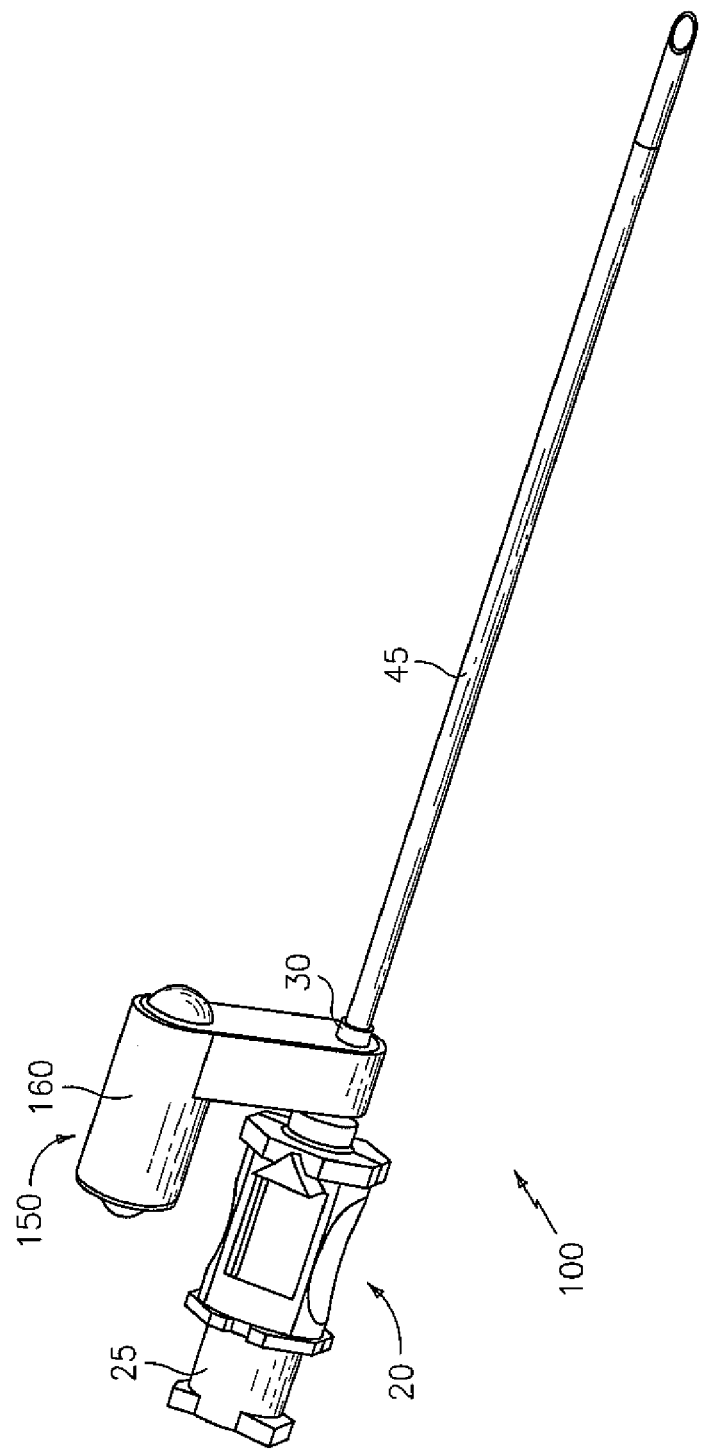
FIG. 4 is a different perspective view of the assembly illustrated in FIG. 3.

Alternatively, housing 60 may slide onto cannula 45 and thus may comprise a "ring" similar to that shown in FIGS. 3 and 4. In such an example, housing 60 would preferably slide onto cannula 45 over one of the ends. In either embodiment, housing 60 may be "friction-fitted" onto the cannula. As should also be appreciated, a cannula mounted housing, whether by snap-fit or slid on, of the type described herein can slide along the cannula, thereby providing the user (e.g. practitioner) a way to move the lightsource closer (or further) to the end 47 as needed.

Rotation of the housing while on the cannula is also provided by the aforementioned "clip-on" or "slide-on" embodiments, and thus provides additional advantages, such as being able to rotate the lightsource to a desired position, a feature not achievable by the prior art.

Reference is now made to FIGS. 3 and 4 for a discussion of the present invention in accordance with a second embodiment. Here, an assembly, generally indicated at 100, comprises cannula/hub assembly 20 and an illumination assembly, generally indicated at 150, preferably comprising a housing 160 and light-emitting element 80 mounted in and/or on housing 160 in a similar manner to which light-emitting element 80 is mounted to or in housing 60. That is, in the embodiment of FIGS. 3 and 4, again light emitting element 80 preferably has one end thereof extending outwardly from housing 160, and again is preferably battery powered and manually operated by way of a push button, such as that positioned on the opposing surface of housing 80 and identical to push button 82.

In this second embodiment, housing 160 comprises an arm 162 that couples (preferably in a removable fashion (such as sliding on in a friction fit), but not necessarily) to a luer lock 30 of assembly 20. Depending on size and weight of the various components that comprise assembly 100, positioning of illuminating assembly 50 on luer lock 30 may provide improved balance of the weighting thereof. Similarly, arm 162 may be snap-fittable (not shown in this embodiment) onto luer lock 30 so as to facilitate the removability thereof. In a similar way, rotation of housing 160 360° is likewise achievable in this embodiment.

Figure 5:
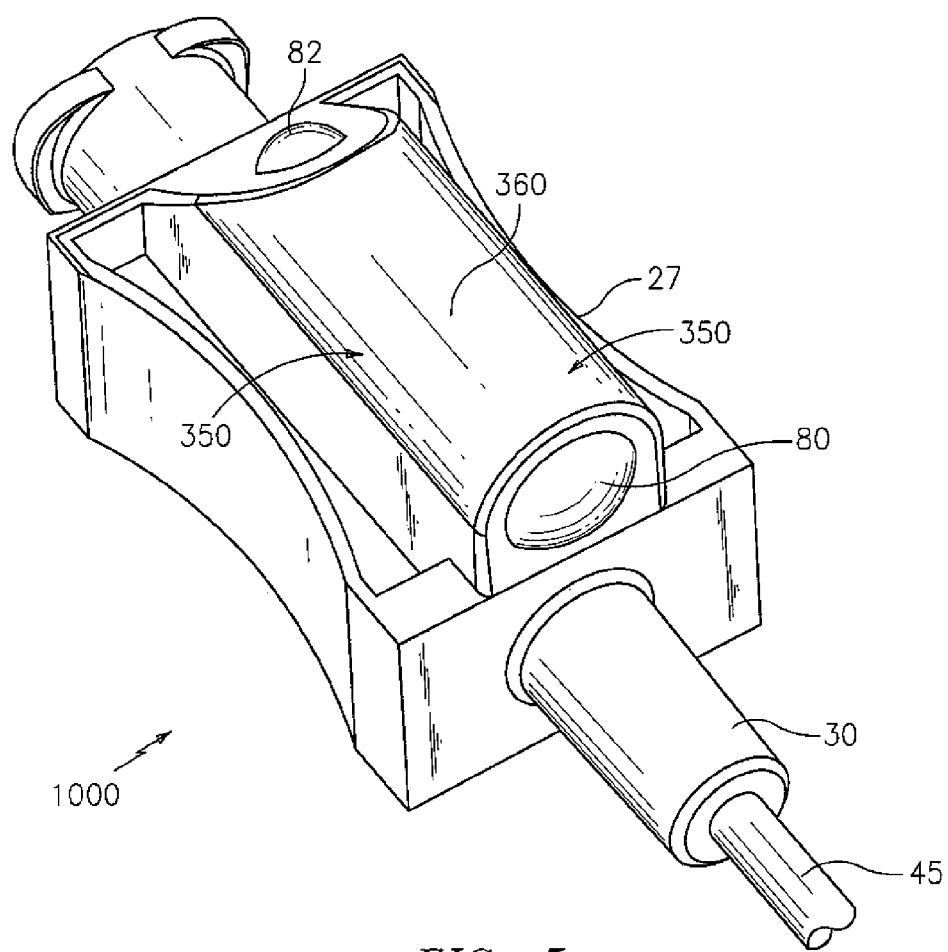
FIG. 5 is a perspective view of an assembly comprising a hub assembly with a molded illumination housing, constructed in accordance with yet a third embodiment of the present invention.
Figure 6:
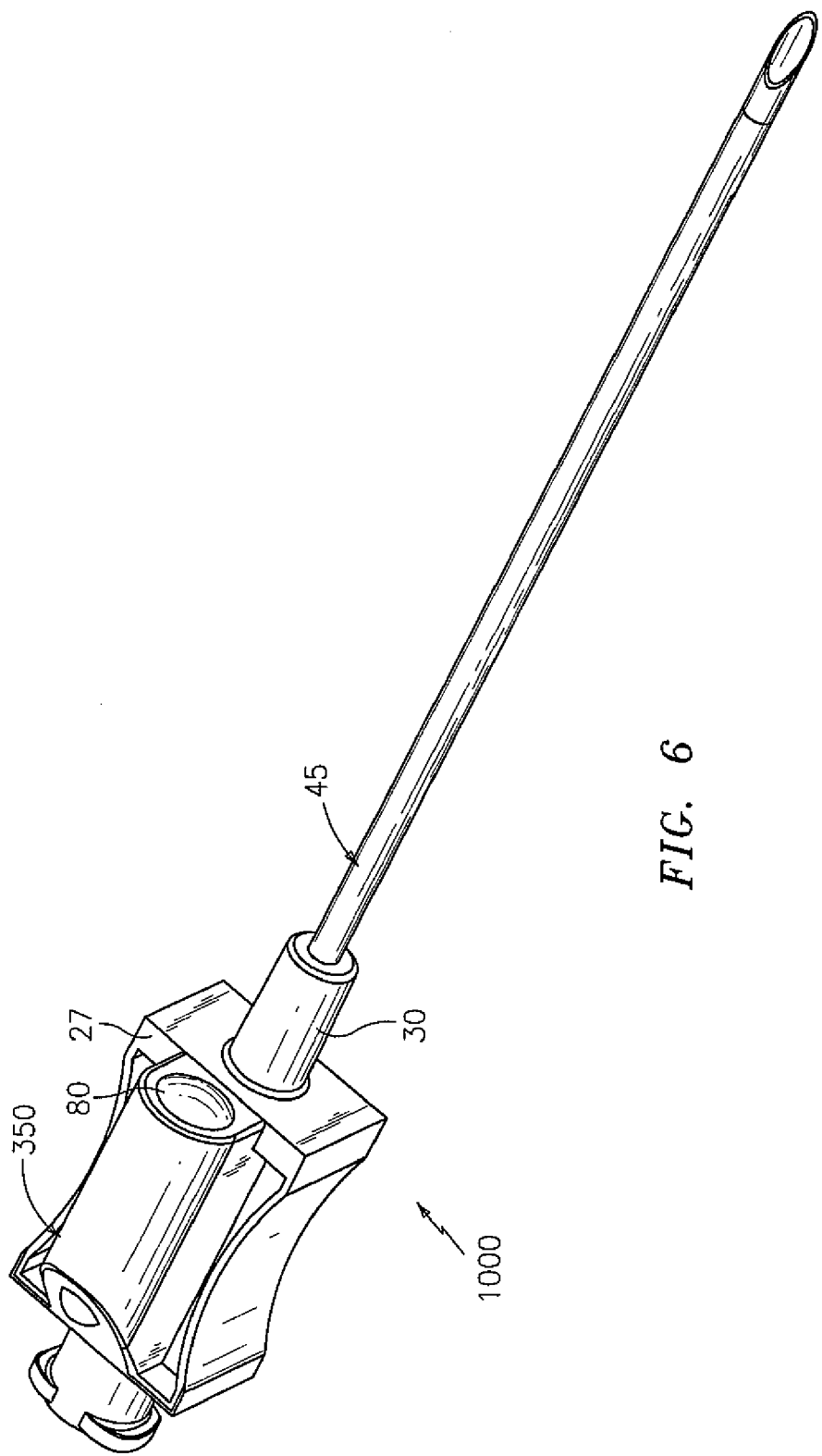
FIG. 6 is taken from the same perspective view as that of FIG. 5, and additionally illustrating the tip of the cannula to best appreciate the preferred orientation of the light-emitting element of the present invention, which is applicable to all embodiments.

In yet a third embodiment of the present invention, an assembly, generally indicated at 1000, comprises a cannula/hub assembly with an integrally formed illumination assembly 350. Specifically, a housing 360 that may be integrally molded with hub 27, thereby forming a cannula/hub assembly not found in the prior art. That is, in this third embodiment, light emitting element 80 may be positioned essentially behind cannula 45 and luer lock 30 to provide yet a further alternative construction. Again, a push button 82 (and appropriate wiring) may be provided for operating light emitting element 80 in a manner similar to those embodiments disclosed above. In this embodiment, if the light emitted from the light-emitting element is sufficient, the actual flashback chamber (e.g. on the opposite side of the hub illustrated in FIGS. 5, 6) can be adequately illuminated.

Figure 7:
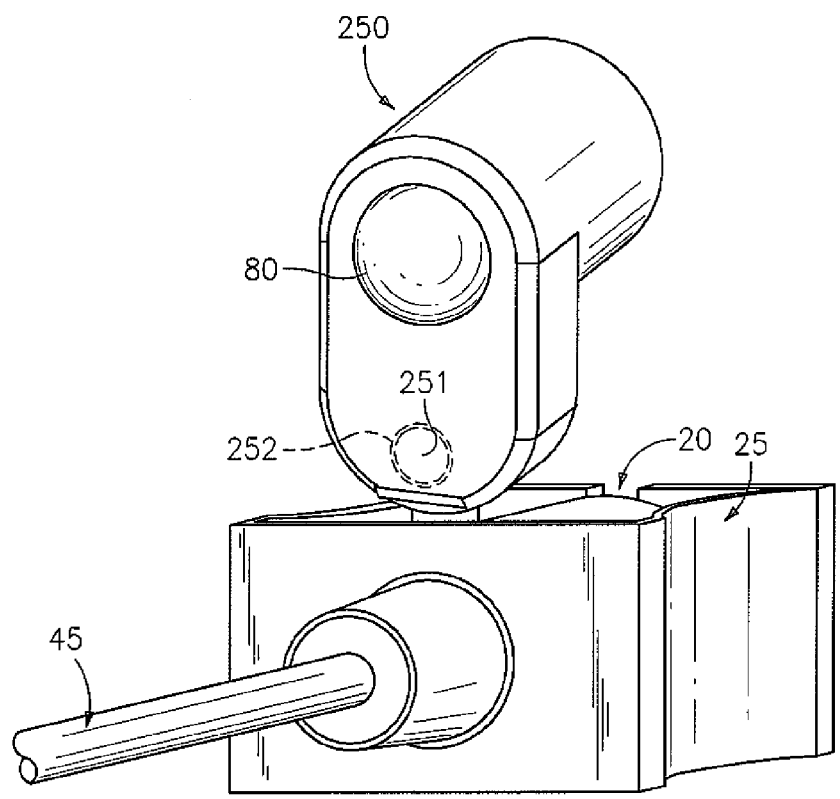
FIG. 7 is a perspective view of showing yet an additional feature/advantage of the present invention.

Lastly, FIG. 7 illustrates yet an additional feature of the present invention, namely an illumination assembly, generally indicated at 250, that provides for pivoting of the light-emitting element. Specifically, FIG. 7 illustrates an illumination assembly pivotably (i.e. swivelably) mounted to the hub 25 itself, by a ball and joint assembly comprising a ball 251 and joint socket 252. Sufficient friction can be provided between the ball and socket to ensure that the assembly 250 does not inadvertently swivel during use. It should be noted that this feature, namely the pivotability of the illumination assembly, is applicable and can be provided in any of the foregoing embodiments, and therefore, the ball and joint assembly as illustrated in this FIG. 7 and disclosed above should be deemed incorporated by reference into any of the aforementioned housings 60 and/or 160. In this way the embodiments disclosed above can swivel, rotate and/or slide.

It can thus be seen that an assembly that comprises an illumination assembly as disclosed above is an improvement over state of the art devices. For example, by providing an illumination arrangement as set forth above, a practitioner can ensure that the entry point of the cannula can remain illuminated even after cannula penetration. Such a construction is extremely advantageous during low-level lighting conditions when cannula illumination throughout the procedure is important.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

While the invention has been particularly shown and described with respect to preferred embodiments thereof, it will be understood by those skilled in the art that changes in form and details may be made therein without departing from the scope and spirit of the invention.

It is also to be understood that the following claims are intended to cover all of the generic and specific features of the invention described herein and all statements of the scope of the invention that as a matter of language might fall there between. For example, reference to a "body" is intended to cover both mammals (e.g. human bodies) and animals (e.g. dogs, cats, etc.).

What is claimed is:

1. An assembly comprising:
  a cannula/hub assembly that withdraws fluids from and/or injects fluids into a person or animal, wherein the cannula/hub assembly comprises a hub having a chamber therein for receiving the fluid and a cannula that is coupled to the hub to permit communication of fluid with the hub, the cannula having a first end securable to or within the hub and a second pointed end dimensioned to permit withdrawal of fluid from and/or injection of fluid into the body by piercing the skin of the person or animal; and
  an illumination assembly comprising:
    a housing; and
    a light-emitting element mounted in and/or on the housing, for emitting directed light to an entry point on the body;
  wherein the illumination assembly is rotatably mounted to the cannula/hub assembly such that the illumination assembly can rotate relative to the cannula/hub assembly without dismounting the illumination assembly from the cannula/hub assembly; and
  wherein the light-emitting element is positioned exteriorly to the cannula/hub assembly so that the location at which the second end of the cannula will enter the skin of the person or animal is illuminateable by the light-emitting element even after the second end has been inserted into the entry point.

2. The assembly as claimed in claim 1, wherein the housing of the illumination assembly is mounted to and rotatable relative to the cannula.

3. The assembly as claimed in claim 2, wherein the housing of the illumination assembly is releasably mounted to the cannula by a snap-fit arrangement.

4. The assembly as claimed in claim 2, wherein the housing of the illumination assembly is pivotable relative to the cannula/hub assembly for directing the light to a selected position on the body; whereby the direction of the light emanating from the light-emitting element can be adjusted relative to the position of the second end of the cannula.

5. The assembly as claimed in claim 1, wherein the housing of the illumination assembly is mounted to and rotatable relative to the hub.

6. The assembly as claimed in claim 5, wherein the housing of the illumination assembly is releasably mounted to the hub by a snap-fit arrangement.

7. The assembly as claimed in claim 5, wherein the housing of the illumination assembly is pivotable relative to the cannula/hub assembly for directing light to a selected position on the body; whereby the direction of the light emanating from the light-emitting element can be adjusted relative to the position of the second end of the cannula.

8. The assembly as claimed in claim 1, wherein the housing of the illumination assembly is friction fittedly mounted to one of the cannula and the hub.

9. A method of withdrawing fluids from and/or injecting fluids into a person or animal with a cannulu/hub assembly while illuminating the location at which the cannula/hub assembly will enter the skin of the person or animal with an illumination assembly rotatably mounted to the cannula/hub assembly, wherein the cannula/hub assembly comprises a hub having a chamber therein for receiving the fluid and a cannula coupled to the hub and having an interior to permit communication of fluid with the hub, the cannula having a first end securable to or within the hub and a second end dimensioned to permit withdrawal of fluid from and/or injection of fluid into the person or animal, and wherein the illumination assembly comprises a housing, a light-emitting element mounted in and/or on the housing; wherein the illumination assembly is at least one of slidable along and rotatable relative to the cannula without dismounting the illumination assembly from the cannula/hub assembly and positioned exteriorly to the cannula/hub assembly, for emitting directed light to the location at which the cannula will enter the person or animal, wherein the method comprises the steps of:
  manually adjusting by at least one of sliding and rotating the position of the light-emitting element relative to the cannula/hub assembly so that the location at which the second end of the cannula will enter the skin of the person or animal remains illuminated after the second end has been inserted into the entry point;

inserting the second end of the cannula into the skin of the person or animal; and one of withdrawing fluids from and/or injecting fluids into the person or animal.

10. The method as claimed in claim 9, comprising the step of:

readjusting the position of the light-emitting element relative to the cannula/hub assembly after the second end of the cannula has been inserted into the person or animal so that the location at which the second end of the cannula entered remains illuminated.

11. An assembly comprising a cannula/hub assembly that withdraws fluids from and/or injects fluids into a person or animal wherein the cannula/hub assembly comprises a hub having a chamber therein for receiving the fluid and a cannula that is coupled to the hub to permit communication of fluid with the hub, the cannula having a first end securable to or within the hub and a second pointed end dimensioned to permit withdrawal of fluid from and/or injection of fluid into the body by piercing the skin of the person or animal; and an illumination assembly comprising:

a housing; and a light-emitting element mounted in and/or on the housing, for emitting directed light to an entry point on the body;

wherein the illumination assembly is slidably mounted to the cannula/hub assembly such that the illumination assembly is slidable along the cannula/hub assembly without dismounting the illumination assembly from the cannula/hub assembly; and wherein the light-emitting element is positioned exteriorly to the cannula./hub assembly so that the location at which the second end of the cannula will enter the skin of the person or animal is illuminateable by the light-emitting element even after the second end has been inserted into the entry point.

12. The assembly as claimed in claim 11, wherein the housing of the illumination assembly is mounted to and slidable along the cannula, whereby the direction of the light emanating from the light emitting element can be adjusted relative to the position of the second end of the cannula.

13. The assembly as claimed in claim 12, wherein the housing of the illumination assembly is releasably mounted to the cannula by a snap-fit arrangement.

14. The assembly as claimed in claim 11, wherein the housing of the illumination assembly is mounted to and slidable along the hub, whereby the direction of the light emanating from the light emitting element can be adjusted relative to the position of the second end of the cannula.

15. The assembly as claimed in claim 11, wherein the housing of the illumination assembly is friction fittedly mounted to one of the cannula and the hub and the illumination assembly can slide along a substantial length of the cannula.

* * * * *